United States Patent
Everman et al.

(10) Patent No.: US 10,667,731 B2
(45) Date of Patent: Jun. 2, 2020

(54) HUMAN PERFORMANCE OXYGEN SENSOR

(71) Applicant: GMECI, LLC, Beavercreek, OH (US)

(72) Inventors: Bradford R. Everman, Haddonfield, NJ (US); Brian Scott Bradke, Brookfield, VT (US)

(*) Notice: Subject to any disclaimer, the term of this patent is extended or adjusted under 35 U.S.C. 154(b) by 426 days.

(21) Appl. No.: 15/492,612

(22) Filed: Apr. 20, 2017

(65) Prior Publication Data
US 2018/0303392 A1 Oct. 25, 2018

(51) Int. Cl.
- *A61B 5/1455* (2006.01)
- *A61B 5/024* (2006.01)
- *A61B 5/01* (2006.01)
- *A61B 5/00* (2006.01)

(52) U.S. Cl.
CPC ........... *A61B 5/14553* (2013.01); *A61B 5/01* (2013.01); *A61B 5/02433* (2013.01); *A61B 5/14552* (2013.01); *A61B 5/6814* (2013.01); *A61B 5/7405* (2013.01); *A61B 5/746* (2013.01)

(58) Field of Classification Search
CPC ........... A61B 5/14553; A61B 5/14552; A61B 5/6814; A61B 5/7405; A61B 5/746
See application file for complete search history.

(56) References Cited

U.S. PATENT DOCUMENTS

| | | | |
|---|---|---|---|
| 3,644,833 A * | 2/1972 | McIntosh | H04B 5/0012 455/351 |
| 4,775,116 A * | 10/1988 | Klein | A61B 5/14553 244/76 R |
| H001039 H * | 4/1992 | Tripp, Jr. | A61B 5/14553 128/201.23 |
| 5,372,134 A * | 12/1994 | Richardson | A61B 5/02422 600/323 |
| 6,498,942 B1 | 12/2002 | Esenaliev | |
| 7,040,319 B1 * | 5/2006 | Kelly | A61M 16/0051 128/204.22 |
| 9,826,941 B1 * | 11/2017 | Serovy | A61B 5/746 |
| 2009/0010474 A1 * | 1/2009 | Ouryouji | H04R 1/1058 381/370 |

(Continued)

FOREIGN PATENT DOCUMENTS

| | | |
|---|---|---|
| KR | 1020050005661 A | 1/2005 |
| WO | 2011010295 A1 | 2/2001 |
| WO | 2011104888 A1 | 9/2011 |

*Primary Examiner* — Eric F Winakur
*Assistant Examiner* — Marjan Fardanesh
(74) *Attorney, Agent, or Firm* — Caldwell Intellectual Propert

(57) ABSTRACT

Systems and methods for measuring oxygenation signals are presented. The method includes positioning an oxygenation measuring system over a side portion of a head of a user, wherein the oxygenation measuring system includes an outer shell, a gel seal coupled to the outer shell, a near-infrared spectroscopy sensor configured to measure oxygenation signals from a user, a printed circuit board coupled to the near-infrared spectroscopy sensor, and a bone conducting transducer. The method further includes measuring the oxygenation signals from the user using the near-infrared spectroscopy sensor, recording data pertaining to the measured oxygenation signals of the user, and comparing the data, using the printed circuit board, with known human performance data.

23 Claims, 5 Drawing Sheets

(56) References Cited

U.S. PATENT DOCUMENTS

2015/0146893 A1\* 5/2015 Kunimoto .............. H04R 5/033
                                                    381/151
2015/0189441 A1\* 7/2015 Oishi ..................... H04R 5/033
                                                    381/309

\* cited by examiner

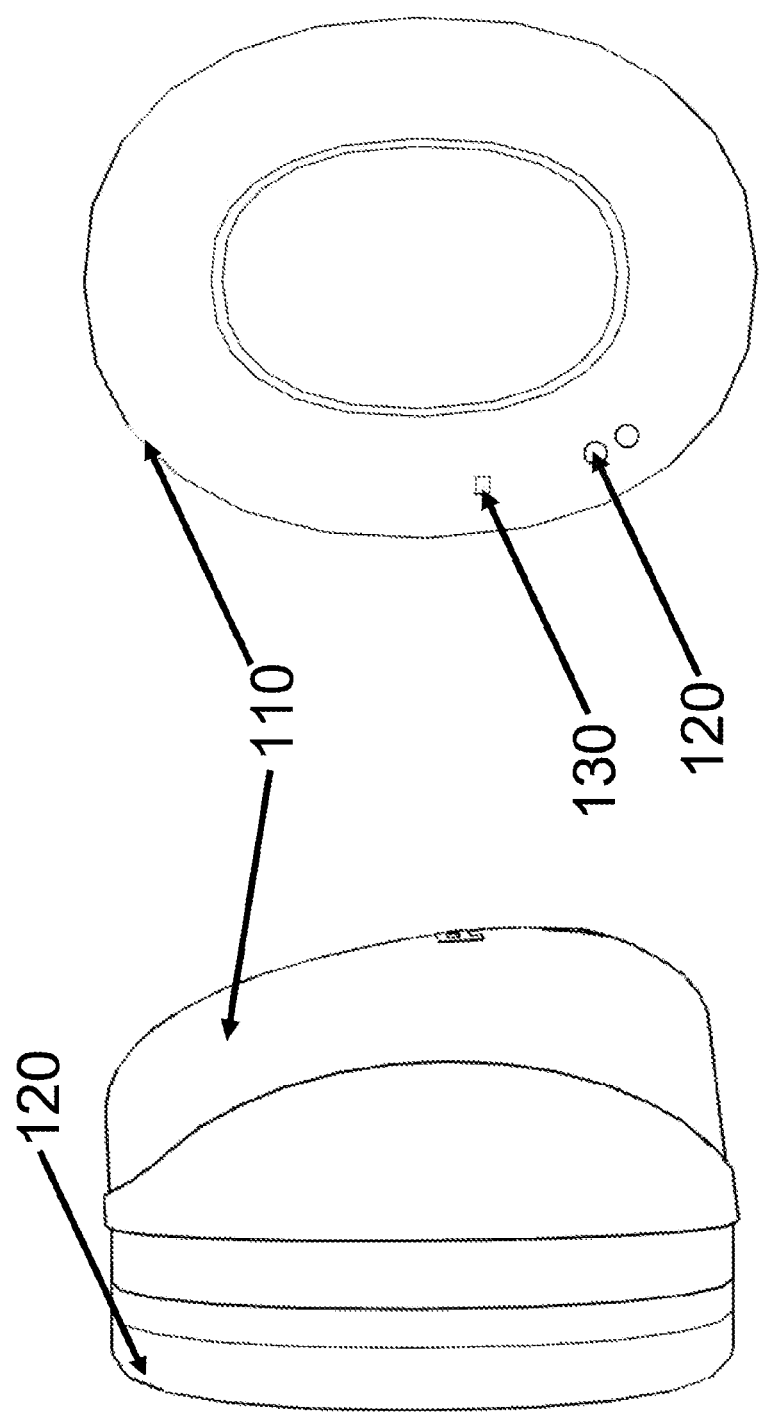

HUMAN PERFORMANCE OXYGEN SENSOR

CLAIM OF PRIORITY

This application is a United States non-provisional application and claims no priority to any previous patent or patent application.

FIELD OF THE EMBODIMENTS

This invention relates to oxygenation sensors and, in particular, to human performance oxygen sensors that can be placed over an ear of a user.

BACKGROUND OF THE EMBODIMENTS

Human oxygenation can determine a plurality of physical characteristics and ailments, including determining whether an individual is on the verge of losing consciousness. Typically, sensors measuring oxygenation are placed on the fingers or foreheads of patients and do not include a means of analyzing the data and alerting the user or a third party of whether an issue has been determined. A means of easily measuring human oxygenation, analyzing the data, and the alerting one or more individuals is thus needed.

Examples of related art are described below:

U.S. Pat. No. 6,498,942 generally describes an optoacoustic apparatus which includes a radiation source of pulsed radiation and a probe having a front face to be placed in close proximity to or in contact with a tissue site of an animal body. The probe further includes a plurality of optical fibers terminating at the surface of the front face of the probe and connected at their other end to a pulsed laser. The front face of the probe also has mounted therein or thereon a transducer for detecting an acoustic response from blood in the tissue site to the radiation pulses connected to a processing unit which converts the transducer signal into a measure of venous blood oxygenation.

International Patent Publication No. WO0110295A1 generally describes an optoacoustic apparatus which includes a radiation source of pulsed radiation and a probe having a front face to be placed in close proximity to or in contact with a tissue site of an animal body. The probe further includes a plurality of optical fibers terminating at the surface of the front face of the probe and connected at their other end to a pulsed laser. The front face of the probe also has mounted therein or thereon a transducer for detecting an acoustic response from blood in the tissue site to the radiation pulses connected to a processing unit which converts the transducer signal into a measure of venous blood oxygenation.

International Patent Publication No. WO2011104888A1 generally describes a pulse oximeter that can be used for adults, children, and newborn infants alike, and can conduct excellent measurements by adjusting the measuring cavity to match finger size. The disclosed pulse oximeter is provided with a measuring cavity for receiving a test site (e.g. a finger) of a subject, a measuring structure that comprises a light emitting part and a light receiving part disposed facing one another across the measuring cavity, and a filling member that is formed from a material that is penetrable by the light being used for measurement, and is added onto an enclosure. The inner curved surface of the filling member has a curvature greater than the outer curved surface thereof, and the filling member changes the curvature of the surface of the interior space of the measuring cavity. By inserting the filling member into the measuring cavity, the gap between the finger and the inner space of the measuring cavity is filled so that the finger is held tightly so as to prevent movement within the interior space of the measuring cavity.

South Korean Patent Publication No. KR1020050005661A generally describes a pulse oximeter and a method thereof to search only the restored signal of an original photoplethysmographic signal (PPG) by suitably removing a motion artifact.

None of the art described above addresses all of the issues that the present invention does.

SUMMARY OF THE EMBODIMENTS

According to an aspect of the present invention, a system for measuring oxygenation signals is presented. The system includes an outer shell, a gel seal coupled to the outer shell, a near-infrared spectroscopy sensor configured to measure oxygenation signals from a user, a printed circuit board, including a processor, coupled to the near-infrared spectroscopy sensor, and a bone conducting transducer.

According to another aspect of the present invention, a method for measuring oxygenation signals is presented. The method includes positioning an oxygenation measuring system over a side portion of a user, wherein the oxygenation measuring system includes an outer shell, a gel seal coupled to the outer shell, a near-infrared spectroscopy sensor configured to measure oxygenation signals from a user, a printed circuit board coupled to the near-infrared spectroscopy sensor, and a bone conducting transducer. The method further includes measuring the oxygenation signals from the user using the near-infrared spectroscopy sensor, recording data pertaining to the measured oxygenation signals of the user, and comparing the data, using the printed circuit board, with known human performance data. According to an embodiment, the sensor rests behind the ear on the neck of the user, over the sternocleidomastoid muscle.

It is an object of the present invention to provide the system for measuring oxygenation signals, wherein the near-infrared sensor includes at least one optical sensor and at least one infrared light emitting diode.

It is an object of the present invention to provide the system for measuring oxygenation signals, wherein one or more of the at least one optical sensor is a near-infrared optical sensor.

It is an object of the present invention to provide the system for measuring oxygenation signals, wherein the printed circuit board is housed within the outer shell.

It is an object of the present invention to provide the system for measuring oxygenation signals, wherein the outer shell includes a material selected from the group consisting of hard plastic and metal.

It is an object of the present invention to provide the system for measuring oxygenation signals, wherein the oxygenation signals include at least one signal selected from the group consisting of: pulse oximetry; pulse; and temperature.

It is an object of the present invention to provide the system for measuring oxygenation signals, wherein the printed circuit board includes a power supply, at least one recording device, and at least one accelerometer.

It is an object of the present invention to provide the system for measuring oxygenation signals, wherein the at least one recording device is configured to store data gathered by the near-infrared spectroscopy sensor.

It is an object of the present invention to provide the system for measuring oxygenation signals, wherein the printed circuit board is configured to compare data collected by the near-infrared spectroscopy sensor and compare it to control data.

It is an object of the present invention to provide the system for measuring oxygenation signals, wherein the printed circuit board is further configured to predict, using data collected from the near-infrared spectroscopy sensor, whether a user is going to experience an impending lack of consciousness.

It is an object of the present invention to provide the system for measuring oxygenation signals, wherein, if the printed circuit board predicts that the user is going to experience an impending lack of consciousness, the printed circuit board sends a signal to the bone conduction transducer to send a signal to the user.

It is an object of the present invention to provide the system for measuring oxygenation signals, wherein the signal is an audible alarm.

It is an object of the present invention to provide the method for measuring oxygenation signals, wherein the near-infrared sensor includes at least one optical sensor and at least one infrared light emitting diode.

It is an object of the present invention to provide the method for measuring oxygenation signals, wherein one or more of the at least one optical sensor is a near-infrared optical sensor.

It is an object of the present invention to provide the method for measuring oxygenation signals, wherein the printed circuit board is housed within the outer shell.

It is an object of the present invention to provide the method for measuring oxygenation signals, wherein the outer shell includes a material selected from the group consisting of hard plastic and metal.

It is an object of the present invention to provide the method for measuring oxygenation signals, wherein the oxygenation signals include at least one signal selected from the group consisting of: pulse oximetry; pulse; and temperature.

It is an object of the present invention to provide the method for measuring oxygenation signals, wherein the printed circuit board includes a power supply, at least one recording device, and at least one accelerometer.

It is an object of the present invention to provide the method for measuring oxygenation signals, further comprising storing the data pertaining to the measured oxygenation signals of the user using the at least one recording device.

It is an object of the present invention to provide the method for measuring oxygenation signals, further comprising predicting, using the printed circuit board, whether a user is going to experience an impending lack of consciousness.

It is an object of the present invention to provide the method for measuring oxygenation signals, further comprising, if the printed circuit board predicts that the user is going to experience an impending lack of consciousness, sending a signal to the user, using the bone conduction transducer.

It is an object of the present invention to provide the method for measuring oxygenation signals, wherein the signal is an audible alarm.

BRIEF DESCRIPTION OF THE DRAWINGS

FIG. 2 shows a front view of a human performance oxygen sensor according to an embodiment of the present invention.

FIG. 3 shows a side view of a human performance oxygen sensor according to an embodiment of the present invention.

DESCRIPTION OF THE PREFERRED EMBODIMENTS

Figure 1:
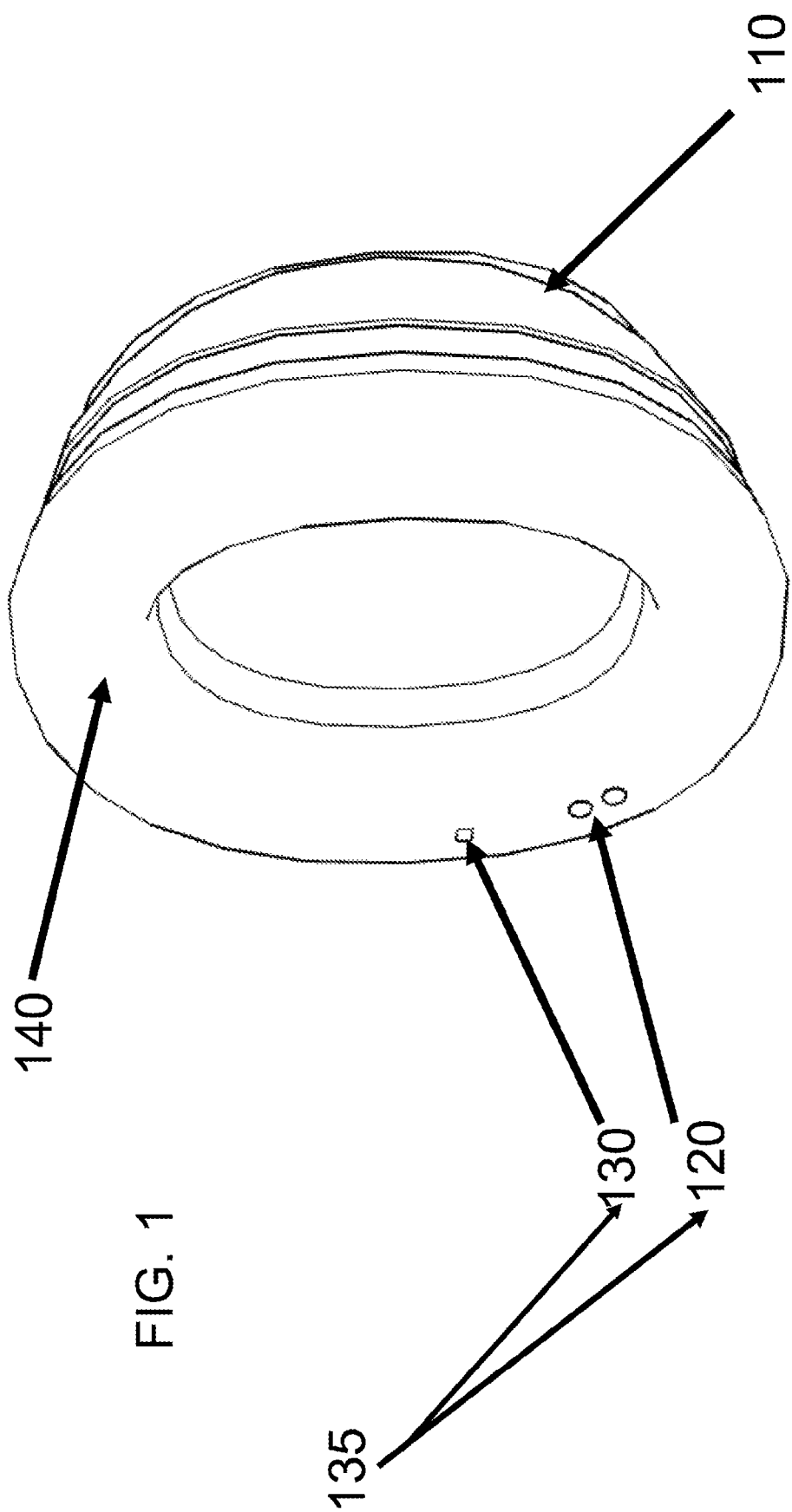
FIG. 1 shows a perspective view of a human performance oxygen sensor according to an embodiment of the present invention.

The preferred embodiments of the present invention will now be described with reference to the drawings. Identical elements in the various figures are identified with the same reference numerals.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

Referring now to FIGS. 1-3, a perspective view (FIG. 1), a front view (FIG. 3) and a side view (FIG. 2) of a human performance oxygen sensor 100 is illustratively depicted, in accordance with an embodiment of the present invention.

Figure 4:
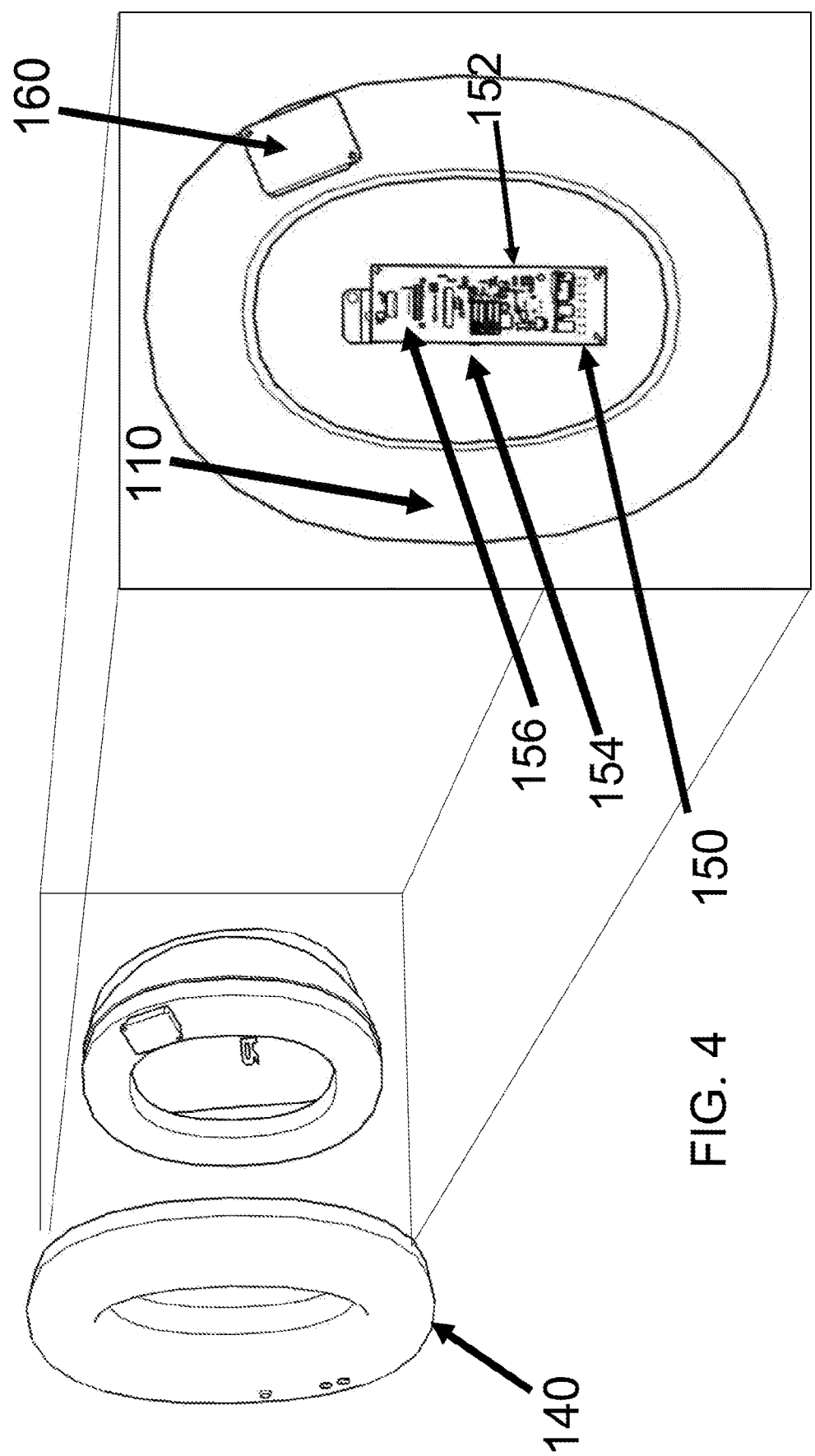
FIG. 4 shows a perspective view of a human performance oxygen sensor having the gel seal and near-infrared spectroscopy sensor removed from the ear cup according to an embodiment of the present invention.

According to an embodiment, the human performance oxygen sensor 100 includes, but is not limited to, an outer shell 110, one or more optical sensors 120, one or more light emitting diodes (LEDs) 130, a gel seal 140, an integrated printed circuit board 150 (shown in FIG. 4), and a bone conducting transducer 160 (shown in FIG. 4).

The one or more optical sensors 120 and/or one or more LEDs 130 may be coupled to the gel seal 140. The one or more optical sensors 120 and/or one or more LEDs may be positioned on the gel seal 140 at a location in contact with a user of the human performance oxygen sensor 100. According to an embodiment, the gel seal 140 is removable from the outer shell 110. It is noted that the gel seal 140 may include any suitable pliable material for placement over a user's ear.

According to an embodiment, one or more of the one or more optical sensors 120 are near-IR sensors. According to an embodiment, the one or more optical sensors 120 and the one or more LEDS 130 form a near-infrared spectroscopy (NIRS) sensor 135. According to an embodiment, the gel seal 140 is placed on an ear cup 110 (shown in FIG. 3) of the outer shell 110.

According to an embodiment, the human performance oxygen sensor 100 measures an individual human being's vital oxygenation signals (e.g., Pulse Oximetry, Pulse, Temperature, etc.). According to an embodiment, the human performance oxygen sensor 100 stores the data gathered from these measurements within a storage medium housed within the human oxygen sensor. According to an embodiment, the human performance oxygen sensor 100 transmits the data to one or more remote storage mediums through one or more wired and/or wireless means. The human performance oxygen sensor 100 compares the data gathered from these measurements to a table of known human performance. According to an embodiment, the printed circuit board 150 may perform any or all of these functions.

According to an embodiment, the outer shell may include a hard plastic, a metal, and/or any other suitable hard material.

Referring now to FIG. 4, a perspective view of a human performance oxygen sensor 100 having the gel seal 140 and NIRS sensor 135 removed from the ear cup 110 is illustratively depicted, in accordance with an embodiment of the present invention.

According to an embodiment, the bone conduction transducer 160 is coupled to the ear cup 110 and is configured to produce an audible alarm. According to an embodiment, when any one signal and/or a combination of signals becomes predictive of impending hypoxia, the human performance oxygen sensor 100 sends a signal through the bone conducting transducer 160 directly to the individual using the human performance oxygen sensor 100.

Based on an individual use case, the signal may be programmed to produce a variety of indications. Possible indications may be, but are not limited to: imminent unconsciousness, substandard oxygenation, erratic pulse, optimum oxygenation, and/or any other suitable indication, while maintaining the spirit of the present invention. According to an embodiment, the human performance oxygen sensor 100 records and stores approximately all of the data measured. This enables in-depth analysis to be performed using a standalone device, e.g., the human performance oxygen sensor 100.

According to an embodiment, the human performance oxygen sensor 100 includes a printed circuit board 150 housed within the outer shell 110. According to an embodiment, the printed circuit board includes a battery 152 or other power supply, one or more recording devices 154, one or more accelerometers 156, one or more processors (configured to perform one or more of the tasks of the printed circuit board 150), and/or any other suitable components, while maintaining the spirit of the present invention. According to an embodiment, the one or more processors are a component of the printed circuit board 150. According to an embodiment, one or more of the NIRS sensor 135 and the bone conduction transducer 160 are coupled to the printed circuit board 150.

Figure 5:
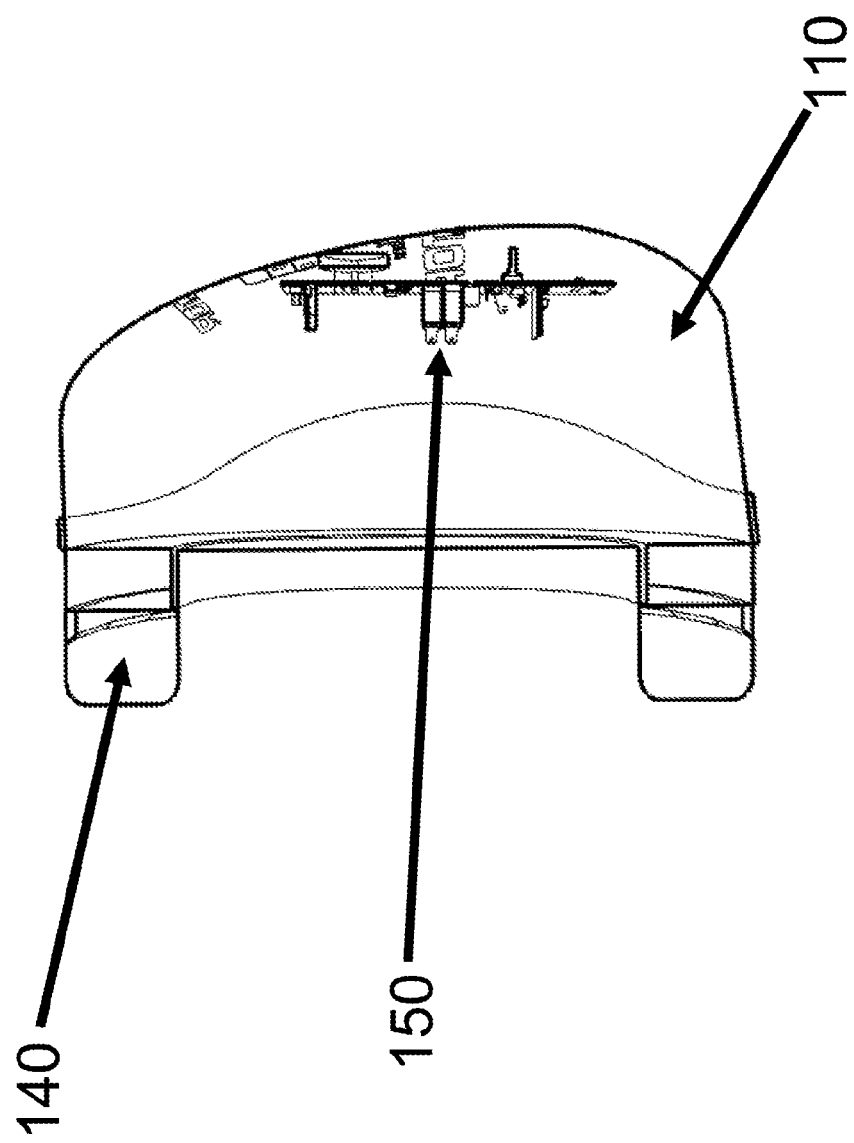
FIG. 5 shows a front sectional view of the human performance oxygen sensor according to an embodiment of the present invention.

Referring now to FIG. 5, a front sectional view of the human performance oxygen sensor 100 is illustratively depicted, in accordance with an embodiment of the present invention.

According to the embodiment shown in FIG. 5, the printed circuit board 150 is housed along an inner wall of the outer shell 110. It is noted, however, that the outer shell 110 may be any suitable shape and that the printed circuit board 150 may be housed in any suitable location within the outer shell 110. According to another embodiment, the printed circuit board 150 is housed external to the outer shell 110.

According to an embodiment, a covering may be placed over the outer shell 110, fully enclosing the printed circuit board 150 within the outer shell 110. The enclosure may include a plastic, a metal, a mesh-type material, and/or any other suitable material while maintaining the spirit of the present invention.

Figure 6:
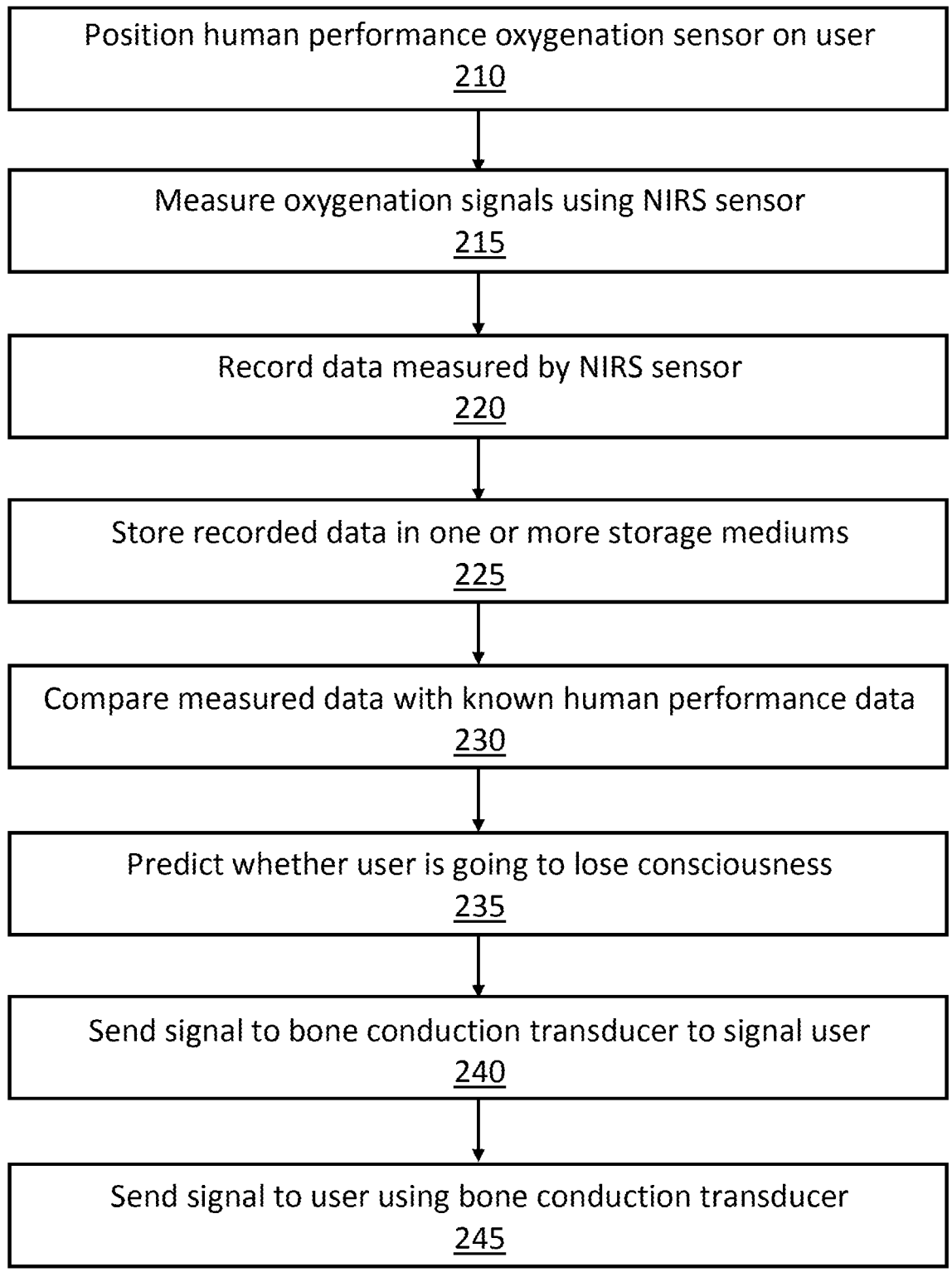
FIG. 6 shows a flowchart of a method of using the human performance oxygen sensor according to an embodiment of the present invention.

Referring now to FIG. 6, a method 200 of using the human performance oxygen sensor 100 is illustratively depicted, in accordance with an embodiment of the present invention.

According to an embodiment, at step 210, the human performance oxygen sensor 100, which functions as an oxygenation measuring system, is positioned over an ear of a user. According to an embodiment, the sensor rests behind the ear on the neck of the user, over the sternocleidomastoid muscle. According to an embodiment, the human performance oxygen sensor includes an outer shell 110, a gel seal 140 coupled to the outer shell 110, an NIRS sensor 135 configured to measure oxygenation signals from the user, a printed circuit board 150 coupled to the near-infrared spectroscopy sensor 135, and a bone conducting transducer 160 coupled to the printed circuit board and positioned over an ear cup 110 portion of the outer shell 110. According to an embodiment, the position of the human performance oxygen sensor 100 enables sufficient contact between the user and the NIRS sensor 135.

According to an embodiment, the NIRS sensor 135 includes at least one optical sensor 120 and at least one light emitting diode 130. According to an embodiment, the printed circuit board 150 includes at least one of a power supply, at least one recording device (which may include one or more storage mediums), a processor, and/or at least one accelerometer. According to an embodiment, the at least one accelerometer may be used to measure movement of the user.

At step 215, the NIRS sensor measures one or more signals from the user pertaining to the oxygenation of the user. The signals may include, but are not limited to, pulse oximetry, pulse, temperature, and/or any other relevant measurement.

According to an embodiment, the NIRS sensor emits near-infrared (red) light into soft tissue and measures how much of the near-infrared light is absorbed by said tissue and how much is reflected. According to an embodiment, the sensing components of the NIRS sensor act essentially as specialized photoresistors. Their resistivity changes as a function of the intensity of light reflected from the tissue. Since well-oxygenated blood (defined as oxygen-bound hemoglobin) absorbs more red light than poorly oxygenated blood, a correlation between the resistivity of the sensor and the blood oxygenation can be ascertained using simple integrated circuitry.

At step 220, data measured from the NIRS sensor 135 is recorded and, at step 225, the recorded data is stored in a storage medium housed within the printed circuit board and/or housed externally.

At step 230, the measured data is compared with known human performance data. According to an embodiment, the known human performance data may include correlation data between sensor resistance and oxygenation. It is noted, however, that the known human performance data may also include other measurable data related to human performance such as, e.g., heart rate data, perspiration data, blood pressure data, and/or any other relevant data related to human performance. According to an embodiment, this comparison is performed by the printed circuit board 150. According to an embodiment, the comparison may be performed by an external device. The external device may be coupled to the human performance oxygen sensor 100 either wirelessly or through a wired connection.

At step 235, the printed circuit board 150 predicts whether a user is going to experience an impending lack of consciousness. According to an embodiment, the printed circuit board constantly monitors blood oxygenation by virtue of the NIRS sensor. According to an embodiment, when oxygenation drops by a predefined percentage, the printed circuit board predicts that the user is going to experience an impending lack of consciousness. According to an embodiment, software for recording g-force, time, and/or other performance data may also be used.

At step 240, if the printed circuit board 150 predicts that the user is going to experience an impending lack of consciousness, the printed circuit board 150 sends a signal to the bone conduction transducer 160 to send a signal, at step 245, to the user to notify the user. According to an embodiment, the signal is an audible alarm. According to an embodiment, the bone conduction transducer sends conducts sound to the inner ear of the user through the user's skull. According to an embodiment, the printed circuit board 150 may further send a signal to a third party device, either wirelessly or through a wired connection, alerting a third party of any relevant predictions made by the printed circuit board 150 while the human performance oxygen sensor 100 is being used.

The human performance oxygen sensor 100 may be used is various fields, according to various embodiments of the present invention. According to an embodiment, the human performance oxygen sensor 100 may be used in conjunction with military aviation. For example, the human performance oxygen sensor may be used for military aviation uses that rely on stored oxygen, e.g., for use in fighter jets and high altitude parachuting. During operation of fighter jets and while performing high altitude parachuting, there is a risk of hypoxia and the inherent need to wear a helmet. The human performance oxygen sensor 100 may be incorporated into such helmets, thus measuring the wearer's vital oxygenation signals while the wearer is wearing the helmet.

According to various embodiments, the human performance oxygen sensor 100 may be used in conjunction with commercial aviation headsets, firefighting uses, and/or in any other suitable field where the measurement of human oxygenation is relevant or necessary for the safety of individuals or for any other relevant reason. According to various embodiments, iterative additional developments of the product include incorporation of a carbon dioxide sensor, reduction in size/weight, removal of the battery 152 to utilize host system available power from the aircraft or vehicle, and/or the inclusion or exclusion of various other suitable components while maintaining the spirit of the present principles.

According to various embodiments, the human performance oxygen sensor may further include incorporation of a pulse oximetry sensor and a carbon dioxide sensor to incorporate the existing product into a fire helmet. The power source and signal may be transmitted to an existing or newly developed two-way radio system in order to allow a fire chief to receive real-time data on all the members of his firefighting force. By transmitting and receiving this data, the fire chief is able to receive real time location and performance data of every single member of his time, optimizing the team's performance.

When introducing elements of the present disclosure or the embodiment(s) thereof, the articles "a," "an," and "the" are intended to mean that there are one or more of the elements. Similarly, the adjective "another," when used to introduce an element, is intended to mean one or more elements. The terms "including" and "having" are intended to be inclusive such that there may be additional elements other than the listed elements.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:

1. A system for measuring oxygenation signals the system comprising:
    an outer shell;
    a gel seal coupled to the outer shell;
    a near-infrared spectroscopy sensor configured to measure at least a human performance datum from a user; and
    a printed circuit board, including a processor, coupled to the near-infrared spectroscopy sensor and configured to send a signal to a user through a bone conduction transducer as a function of the at least a human performance datum.

2. The system as recited in claim 1, wherein the near-infrared spectroscopy sensor includes at least one optical sensor and at least one infrared light emitting diode.

3. The system as recited in claim 2, wherein one or more of the at least one optical sensor is a near-infrared optical sensor.

4. The system as recited in claim 1, wherein the printed circuit board is housed within the outer shell.

5. The system as recited in claim 1, wherein the outer shell includes a material selected from the group consisting of hard plastic and metal.

6. The system as recited in claim 1, wherein the human performance datum include at least one measurement selected from the group consisting of: pulse oximetry; pulse; and temperature.

7. The system as recited in claim 1, wherein the printed circuit board includes one or more components selected from the group consisting of:
    a power supply;
    at least one recording device; and
    at least one accelerometer.

8. The system as recited in claim 7, wherein the at least one recording device is configured to store data gathered by the near-infrared spectroscopy sensor.

9. The system as recited in claim 1, wherein the printed circuit board is configured to compare data collected by the near-infrared spectroscopy sensor and compare it to control data.

10. The system as recited in claim 9, wherein the printed circuit board is further configured to predict, using data collected from the near-infrared spectroscopy sensor, whether a user is going to experience an impending lack of consciousness.

11. The system as recited in claim 10, wherein, if the printed circuit board predicts that the user is going to experience an impending lack of consciousness, the printed circuit board sends a signal to the bone conduction transducer to send a signal to the user.

12. The system as recited in claim 11, wherein the signal is an audible alarm.

13. A method for measuring oxygenation signals comprising:
    positioning an oxygenation measuring system over a side portion of a head of a user, the oxygenation measuring system including:
        an outer shell;
        a gel seal coupled to the outer shell;
        a near-infrared spectroscopy sensor configured to measure at least a human performance datum from a user;
        a printed circuit board coupled to the near-infrared spectroscopy sensor; and
        a bone conducting transducer;
    measuring the at least a human performance datum from the user using the near-infrared spectroscopy sensor;

recording data pertaining to the at least a measured human performance datum of the user;

comparing the data, using the printed circuit board, with known human performance data; and transmitting a signal to a user through the bone conducting transducer as a function of the at least a measured human performance datum.

14. The method as recited in claim 13, wherein the near-infrared spectroscopy sensor includes at least one optical sensor and at least one infrared light emitting diode.

15. The method as recited in claim 14, wherein one or more of the at least one optical sensor is a near-infrared optical sensor.

16. The method as recited in claim 13, wherein the printed circuit board is housed within the outer shell.

17. The method as recited in claim 13, wherein the outer shell includes a material selected from the group consisting of hard plastic and metal.

18. The method as recited in claim 13, wherein the human performance datum include at least one measurement selected from the group consisting of pulse oximetry; pulse; and temperature.

19. The method as recited in claim 13, wherein the printed circuit board includes:

a power supply;

at least one recording device; and at least one accelerometer.

20. The method as recited in claim 19, further comprising storing the data pertaining to the measured oxygenation signals of the user using the at least one recording device.

21. The method as recited in claim 13, further comprising predicting, using the printed circuit board, whether a user is going to experience an impending lack of consciousness.

22. The method as recited in claim 21, further comprising, if the printed circuit board predicts that the user is going to experience an impending lack of consciousness, sending a signal to the user, using the bone conduction transducer.

23. The method as recited in claim 22, wherein the signal is an audible alarm.

* * * * *